US00PP31081P2

(12) United States Plant Patent
Chen et al.

(10) Patent No.: US PP31,081 P2
(45) Date of Patent: Nov. 19, 2019

(54) PEACH TREE NAMED 'RICH JOY'

(50) Latin Name: ***Prunus persica* (L.) Batsch.**
Varietal Denomination: Rich Joy

(71) Applicant: The United States of America, as Represented by the Secretary of Agriculture, Washington, DC (US)

(72) Inventors: Chunxian Chen, Byron, GA (US); William R. Okie, Warner Robins, GA (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 16/350,121

(22) Filed: Sep. 27, 2018

(51) Int. Cl.
*A01H 5/08* (2018.01)
*A01H 6/74* (2018.01)

(52) U.S. Cl.
USPC ..... Plt./198

(58) Field of Classification Search
USPC ..... Plt./194, 187, 198
See application file for complete search history.

*Primary Examiner* — Susan McCormick Ewoldt
(74) *Attorney, Agent, or Firm* — John D. Fado; Ariel L. Atkinson

(57) ABSTRACT

A new and distinct variety of peach tree, denominated 'Rich Joy', has firm, freestone, melting, yellow flesh fruit with normal acidity, rich flavor, good eating quality, and long shelf life on trees and after harvesting. The fruit typically ripen about one week after 'Julyprince' in mid-July in Byron, Ga., have a high percentage of red blush with an attractive yellow ground color on skin surface, and usually are almost round with a slightly prominent suture. The tree is moderately vigorous and semi-spreading in growth habit, has self-fertile showy pink flowers, and regularly bears heavy annual crops. This variety has a winter chilling requirement estimated at approximately 850 chill hours and is suited for high chill areas.

4 Drawing Sheets

Latin name of the genus and species of the plant claimed: 'Rich Joy' is a peach tree that is a *Prunus persica* (L.) Batsch.

Variety denomination: The new peach tree is of the variety denominated 'Rich Joy'.

BACKGROUND OF THE NEW PLANT

The present invention relates to a new and distinct variety of fresh-market peach designated 'Rich Joy' and botanically known as *Prunus persica* (L.) Batsch. This new peach tree is adapted to a Southeastern subtropical climate with high chill in winters. 'Rich Joy' variety resulted from a hand-pollinated cross between 'Flameprince' (unpatented) yellow peach, which was used as the seed parent, and BY87P0943 (unpatented, an advanced selection) yellow peach, which was used as the pollen parent. 'Rich Joy' variety was obtained by hybridizing and propagated by grafting on 'Guardian'® rootstock trees. Its unique fruit characteristics and desired ripening season make it worthy for commercial fresh fruit production. Clonal plants were asexually propagated from the original 'Rich Joy' tree by grafting in Byron, Ga. These asexually propagated plants, along with all characteristics of the tree and the fruit, remained true-to-type to the original 'Rich Joy' tree. There are no known effects of the standard rootstock on the scion cultivar characteristics.

'Rich Joy', produces firm, freestone, melting, yellow-flesh fruit with normal acidity, rich flavor, good eating quality, attractive blush, and long shelf life on trees and after harvesting, ripening in July in Byron, Ga. 'Rich Joy' is a promising candidate for commercial success in that it has large and attractive fruit with long on-tree life and shelf life after harvesting.

Byron, Ga. is under a subtropical climate. Winters are short, mild and with little snow; summers are long, hot and humid. The average January low temperature is about 1.2° Celsius and the average July high temperature is about 33.2° Celsius. The hours with temperatures below 7° Celsius vary often between 600 and 1200 hours per year. There are about 67 rainy days per year. Average annual precipitation (rainfall) is 1182.88 millimeter (46.57 inch) with great monthly and yearly variabilities and frequent thunderstorms in summers.

SUMMARY OF THE INVENTION

The new and distinct variety 'Rich Joy' peach tree blooms mid to late March, approximately with or slightly after 'Flameprince' (unpatented) peach trees in Byron, Ga. The estimated chilling requirement, based on bloom time, is approximately 850 chill hours. The blooming period and the blooming date are dependent on climatic conditions. The flower anthers are yellow, and leaf glands are reniform, common characteristics of many standard peach varieties.

The first fruit of 'Rich Joy' ripen generally in mid-July in Byron, Ga., in the season of 'Cresthaven' (unpatented) and 'Early Augustprince' (unpatented) and approximately one week after 'Julyprince' (unpatented) and two weeks before 'Flameprince' (unpatented). 'Rich Joy' trees are vigorous and productive, size well, and crop reliably. 'Rich Joy' fruit tend to have rich flavor, good eating quality, slow melting texture, and more blush coverage (approximately 85% red skin) than 'Cresthaven' (unpatented) and 'Early Augustprince' (unpatented). There is some red pigmentation in the yellow flesh at the pit if allowed to mature on the tree. The potential for commercial production of fresh 'Rich Joy' fruit is high, due to its long shelf life on trees and after harvest, attractive red skin over yellow ground color, and rich flavor.

BRIEF DESCRIPTION OF THE PHOTOGRAPHS

The accompanying drawings are color photographs that are as nearly true as it is reasonably possible to make in a color illustration of this type:

Figure 1:
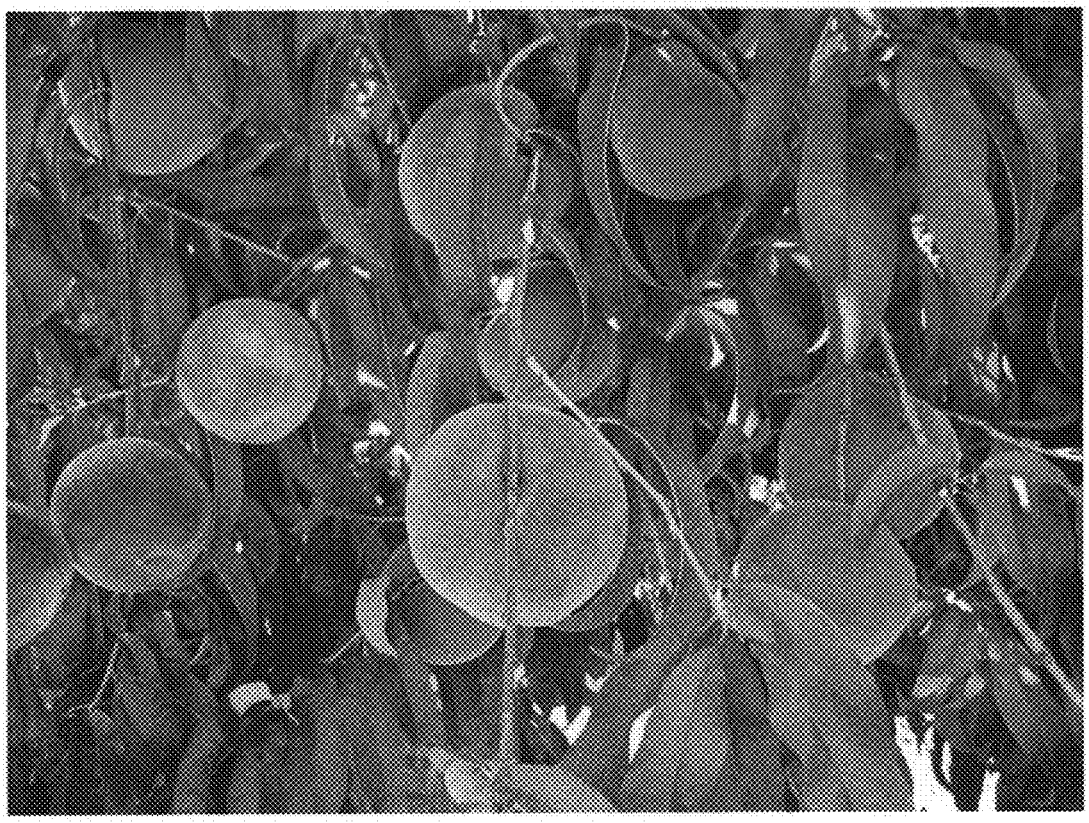
FIG. 1 is a color photograph that shows a close view of typical fruits of the new variety 'Rich Joy' at ripening time at Byron, Ga.
Figure 2:
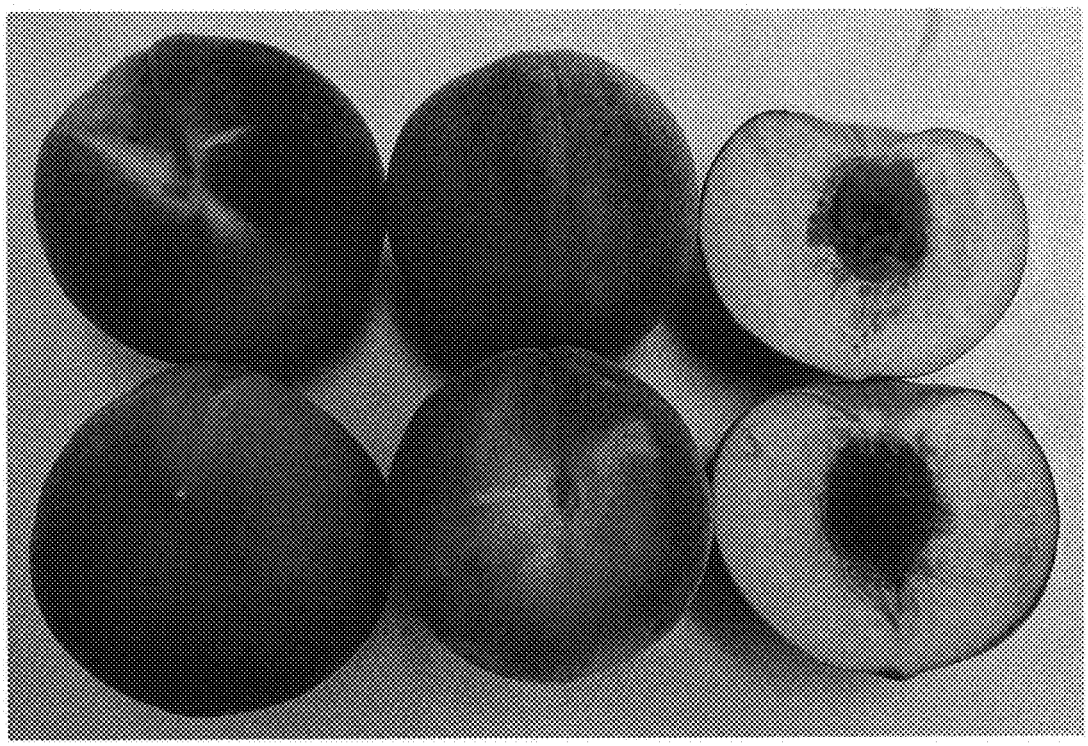
FIG. 2 is a color photograph that shows an attractive shape, exterior coloration, flesh, and pit of five specimens of 'Rich Joy' fruit in a stem end view, a blossom end view, a side view showing the suture, a side view showing the back, and a fruit longitudinally cut into halves without and with the pit. Fruit are picked from an orchard at Byron, Ga.
Figure 3:
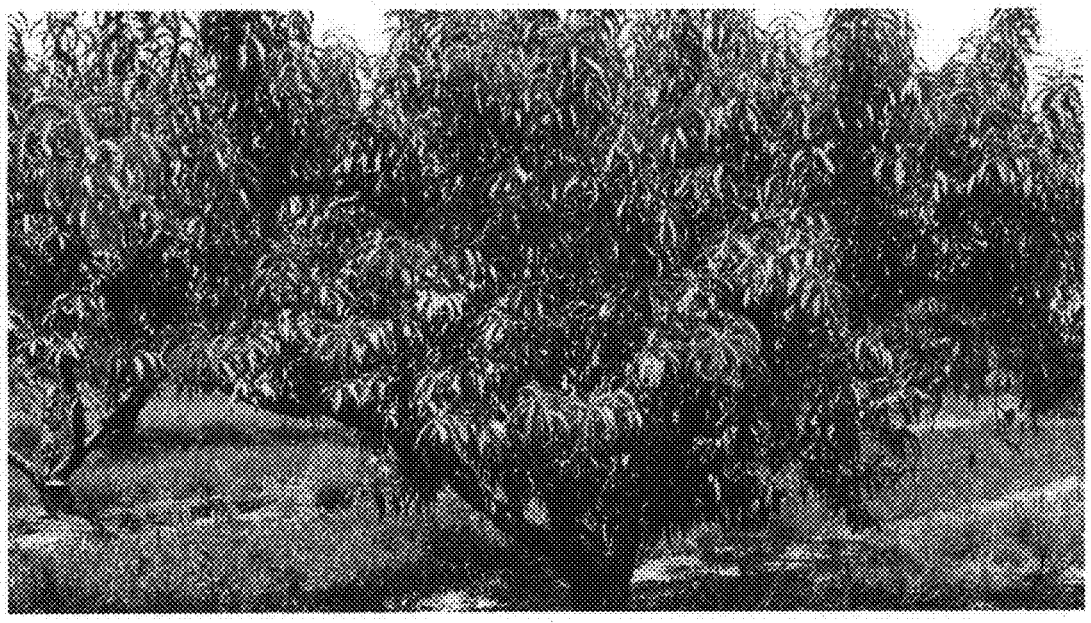
FIG. 3 is a color photograph that shows the typical semi-spreading architecture of an 8-year-old tree of the new variety 'Rich Joy' at Byron, Ga.
Figure 4:
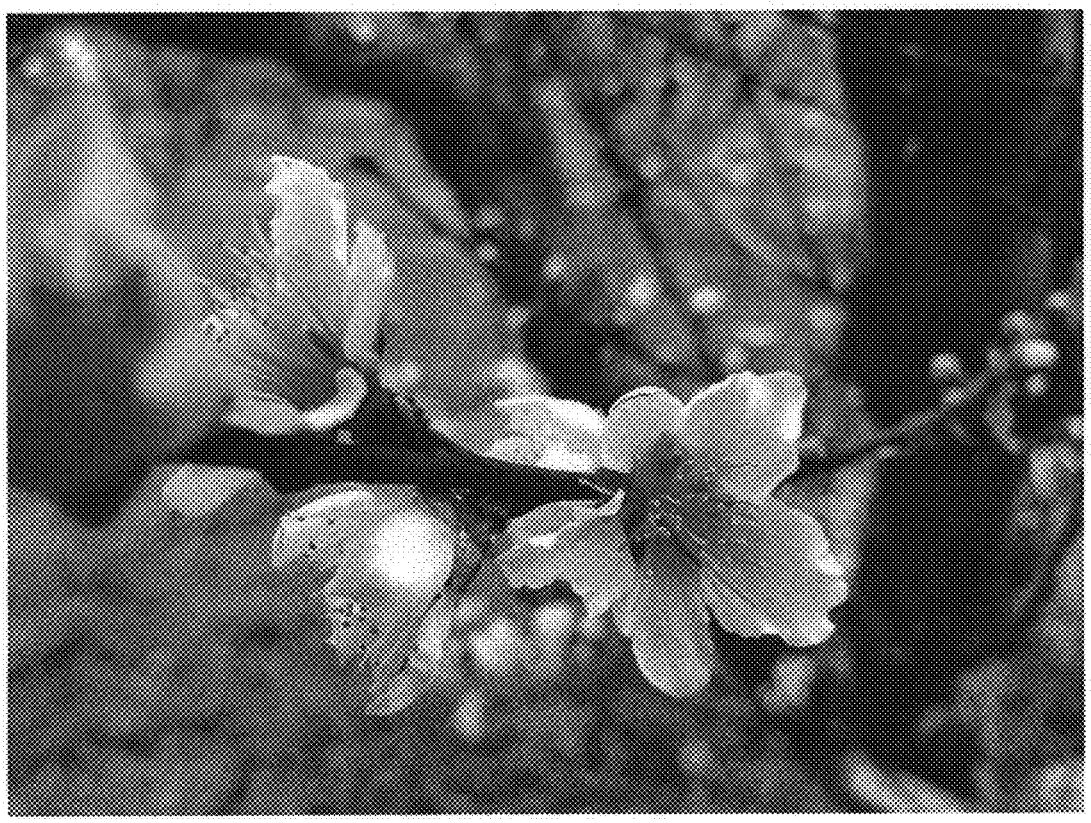
FIG. 4 is a color photograph that shows typical showy flowers of the new variety at Byron, Ga.

Due to photographical light, chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil types, cultural practices, climatic conditions, growing seasons, and development stages. Referring more specifically to the detailed botanical description of this new and distinct variety of yellow peach tree, the following was observed on 11-year-old trees of the variety grafted on 'Guardian'® rootstock under the ecological conditions prevailing at the orchards located at the town of Byron, Ga., USA. All major color code designations are by reference to The Royal Horticultural Society (R.H.S.) Colour Chart (Fourth Edition).

Tree:

*Size*.—Generally considered large when trained to an open vase form. The height and width of 11-year-old tree are 2.9 meters and 4.9 meters, respectively, including current season shoots.

*Spread*.—Grown to a vase shape with summer and winter pruning to keep the tree open to get strong fruiting wood in the lower center.

*Vigor*.—Considered moderately vigorous. Approximately 1.0 to 1.5 meters in height and width of growth occurs in the orchards at Byron, Ga. Trees respond typically to irrigation and fertilization.

*Productivity*.—Very productive and regular, every year. Fruit set is spaced by thinning to develop the remaining fruit into desired market size. The fruit number varies with the prevailing climatic conditions and cultural practices.

*Bearer*.—Very regular without alternate bearing observed. The fruit is distributed homogenously on both short and long shoots and must be thinned to avoid limb breakage and obtain large fruit size.

*Form*.—Semi-spreading, but easily pruned to vase shape.

*Density*.—Considered dense. Pruning is required to open the tree center to promote sunlight entrance for enhancing fruit color and sugar.

*Hardiness*.—Hardy with respect to typical Georgia winters.

*Chilling requirement*.—Estimated endodormancy chilling requirement is approximately 850 chill hours based on time of bloom and leafing in relation to standard varieties.

Trunk:

*Size*.—Approximately 32.5 cm in diameter at a height of approximately 30.0 cm on the 11-year-old trees at Byron, Ga.

*Bark texture*.—Generally smooth, but changes to light shaggy as tree ages.

*Bark color*.—RHS Grey Group 201D, slightly darker than the outside of lenticel color. Bark crack's color is RHS Greyed-Orange Group 173C.

*Lenticels*.—Moderately low number, approximately 1 to 3 per square cm of surface area of trunk; and the average lenticel length and width of lenticels are approximately 8.6 millimeters and 3.1 millimeters, respectively.

*Lenticel color*.—The outside of lenticels is RHS Grey Group 201A, whereas the inside is RHS Greyed-Orange Group 173C.

Branches:

*Size*.—Average as compared to other peach varieties. Strong growth of scaffold branches. The current season mature fruiting branches have a diameter from 9.0 to 13.0 millimeters, and the average diameter is 10.3 millimeters. Tree growth and structure permits easier and faster winter pruning.

*Surface texture*.—Relatively smooth, numerous lenticels but smaller size than found on trunk and old scaffolds. Roughness increases with age.

*Crotch angles*.—Moderate to wide angles within the normal range of standard varieties for a semi-spreading tree after proper summer and winter pruning.

*Internode length*.—Approximately 1.4 to 2.6 centimeters with the average of 2.0 centimeters.

*Color of mature branches*.—RHS Grey Group 201B at the upper part (sunny side) of the shoots and RHS Greyed-Orange Group 177B at the lower part (shady side) of the shoots.

*Color of current season shoots*.—RHS Greyed-Orange Group 166A at the upper part (sunny side) of the shoots and RHS Yellow-Green Group 145B at the lower part (shady side) of the shoots.

Leaves:

*Size*.—Considered medium to large for the species.

*Length*.—Approximately 165.0 to 196.0 millimeters with the average of 181.1 millimeters, not including the petiole.

*Width*.—Approximately 33.7 to 43.3 millimeters with the average of 38.4 millimeters.

*Thickness*.—Regular and average for commercial varieties, approximately 0.15 to 0.46 millimeters with the average of 0.20 millimeter, not noticeably unusual.

*Form*.—Lanceolate.

*Apex*.—Acute.

*Margin*.—Serrulate.

*Base*.—Acute.

*Surface.*—Upper, glabrous; Lower, medium large veins that are pinnately netted.

*Color.*—Regular green, slightly different in seasons. In early shoot growth, both upper and lower leaf surfaces are RHS Yellow-Green 151A. In late season, upper leaf surface is RHS Green Group 137A and lower surface is RHS Yellow-Green Group 146B. Leaf vein is RHS Yellow-Green Group 150D.

*Glands.*—Reniform. Usually 2-3 on lower leaf blade and 2-3 on petioles. The average length is approximately 0.9 millimeters and width 0.3 millimeters. Color is RHS Yellow-Green Group 146B.

*Petiole.*—Approximately 9.8 to 13.5 millimeters length, approximately 1.79 to 2.31 millimeters diameter. Color is RHS Yellow-Green Group 146B.

*Stipules.*—Medium, equal to most commercial peach varieties, visible on younger leaves, usually about 2 per leaf, and abscising just before leaf becomes full size in summer growth. Color at full size is RHS Yellow-Green Group 151A before abscising.

*Leaf blade incisions.*—Serrulate.

*Arrangement.*—Alternate.

Flowers:

*Flower buds.*—The form of flowers buds changes as blooming approaches, with variable dimensions. They are conic at pre-floral stage and approximately 6.0 to 7.8 millimeters long and 3.3 and 4.6 millimeters wide. The bud color in mid-winter is RHS Greyed-Green Group 198B. The abundance is very high due to shorter than average internode length. Most buds set fruit in absence of spring frosts and show little evidence of bud drop.

*Hardiness.*—Hardy with respect to Georgia winters.

*Date of bloom.*—Mid-late March depending on winter chilling and amount of warm weather.

*Blooming time.*—Considered medium-late in bloom relative to other commercial peaches in central Georgia. Typically blooms with 'Flameprince'.

*Duration of bloom.*—Approximately 6 to 14 days. This characteristic varies significantly with amount of winter chilling as well as temperatures during bloom.

*Bloom quantity.*—Generally abundant, with a good distribution.

*Flower bud frequency.*—Generally two flower buds per node, but occasionally one.

*Fragrance.*—Undetectable or faint floral scent.

*Type.*—Showy.

*Size.*—Approximately 30.8 to 43.0 millimeters in diameter at full bloom, with the average of 37.3 millimeters.

*Petal.*—Size: Generally considered large. Length: approximately 15.1 to 20.1 millimeters with the average of 17.8 millimeters. Width: approximately 9.7 to 14.2 millimeters with the average of 12.1 millimeters. Form: generally round-shaped. Count: almost always five. Arrangement: Texture: smooth, soft and glabrous. Color: RHS Red-Purple Group 63D in the upper surface and RHS Red-Purple Group 62C in the lower surface. Margins: Generally slightly undulating. Apex: generally round and curved-shaped.

*Pedicel.*—Length: approximately 3.5 to 4.8 millimeters with the average of 4.3 millimeters. Diameter: approximately 1.5 to 1.9 millimeters with the average of 1.7 millimeters.

*Calyx cup.*—Diameter: approximately 16.1 to 19.3 millimeters with the average of 17.3 millimeters. Color: RHS Green Group 143C at the interior surface and Greyed Red Group 178A at the exterior surface.

*Sepals.*—Number: generally five sepals. Length: approximately 6.8 to 9.2 millimeters with the average of 7.6 millimeters. Width: approximately 5.2 to 6.4 millimeters with the average of 5.8 millimeters. Color: RHS Greyed-Purple 187A.

*Stamen number.*—Approximately 31 to 50 stamens per flower with the average of 40.7.

*Anthers.*—Color: RHS Yellow Orange 16A at opening.

*Pollens.*—Generally abundant and approximately RHS Yellow-Orange 18A.

*Filaments.*—Length at opening: approximately 10.7 to 15.5 millimeters with the average of 13.1 millimeters. The length of filaments is generally higher than that of pistils. Color: RHS Red Group 36C.

*Pistil.*—Number: Usually one. Length: approximately 10.3 to 13.2 millimeters with the average of 11.5 millimeters and generally equal to stamen length, if not slightly smaller. Color: RHS Yellow Group 2D (Pistil tip color is RHS Green Group 138D).

Fruit:

*Maturity when described.*—Tree ripe, Jul. 17, 2018 at Byron, Ga., and firm in ripe conditions.

*Date of harvest.*—Vary slightly with the prevailing climatic conditions. The picking starts first on Jul. 17, 2018, and until Jul. 23, 2018.

*Size.*—Generally uniform, large size. Weight: approximately 150 to 210 grams with the average of 170.7 grams. Equatorial diameter: approximately 67.6 to 75.2 millimeters with the average of 70.7 millimeters. Polar diameter (from stem to distal end): approximately 67.4 to 74.8 millimeters with the average of 70.4 millimeters. This characteristic highly depends on fruit number per tree, soil type, climatic conditions, and cultural practices, and therefore is not particularly distinctive of the variety.

*Peduncle.*—Length: approximately 4.5 to 8.5 millimeters with the average of 6.4 millimeters. Width: approximately 3.2 to 4.1 millimeters with the average of 3.6 millimeters. Color: RHS Green Group 142D.

*Longitudinal section form.*—Generally round.

*Transverse section through diameter.*—Generally round with a slight ridge on suture.

*Suture.*—Slightly ridged with a slight crease.

*Ventral surface.*—Generally rounded.

*Shape of fruit base.*—Slightly Truncate.

*Apex.*—Generally round, sometimes with a slightly cuspidate tip.

*Crater at stem attachment.*—Flaring oval to the suture. Depth: approximately 12.7 to 17.7 millimeters with the average of 14.8 millimeters. Width at top: approximately 18.0 to 27.0 millimeters with the average of 23.1 millimeters at top. Width at bottom (pedicel attachment): approximately 3.9 to 6.1 millimeters with the average of 5.1 millimeters.

*Skin.*—Thickness: generally medium in comparison to commercial peach varieties. Texture: generally typical of commercial peach varieties. Tenacity: Tenacious. Color: RHS Grey-Purple 186A, approximately 80% to 95% of skin. Fruit exposed to sunlight likely have a higher degree of enhanced skin color. Ground color: RHS Yellow 5C. Tendency to crack: None observed. Taste: No astringency observed. Epidermis: Typical short pubescence.

*Flesh*.—Ripens: evenly within each fruit. Texture: smooth, firm, slow melting when fully ripe. Fibers: very fine, small, tender, and abundant. Aroma: typical of commercial peach varieties. Eating quality: excellent rich flavor with typical acidity. Soluble solids content: approximately 8.6 to 13.7° Brix with the average of 11.5° Brix when at approximately 3.4 to 6.2 kgf of penetrometer firmness (the average is 4.6 kgf) with a standard 5.16-inch tip following a seven-day post-harvest storage protocol. This characteristic varies slightly with fruit number per tree, climatic conditions, cultural practices, and ripening stages. Juice: moderately abundant. Color: RHS Yellow-Orange 15C. Color of red flecks within flesh: RHS Orange-Red 34A. Color of flesh at pit: RHS Red 46A. Browning by oxidation: none observed on tree ripe fruit beginning to soften. Amygdalin: none undetected.

Stone:

*Type*.—Freestone.

*Size*.—Generally medium large. The stone size varies upon the tree vigor, crop load and prevailing growing conditions. Length: approximately 33.1 to 37.2 millimeters with the average of 35.1 millimeters. Width: approximately 22.7 to 26.8 millimeters with the average of 25.1 millimeters. Diameter: approximately 18.2 to 22.8 millimeters with the average of 19.5 millimeters.

*Wall thickness*.—Approximately 5.8 to 7.6 millimeters with the average of 6.7 millimeters.

*Color*.—RHS Red-Purple 59A when flesh is freshly cut.

*Form*.—Oblong

*Base*.—Truncate.

*Apex*.—Acute with cuspidate tip.

*Sides*.—Unequal.

*Surface*.—Generally furrowed toward ventral edge.

*Tendency to split*.—None observed.

*Kernel*.—Viable if stratified upon removal from fruit at harvest, and without drying. Taste: bitter. Size: Considered medium large. Length: approximately 15.9 to 19.0 millimeters with the average of 17.6 millimeters. Width: approximately 10.2 to 12.4 millimeters with the average of 10.9 millimeters. Thickness: approximately 5.0 to 6.6 millimeters with the average of 5.7 millimeters. Form: generally ovate with acute tip and obtuse base. Color: RHS Yellow-Orange 16C.

Use of the fruit: Fresh, dessert.

Keeping quality: Excellent after about two weeks at approximately 2 to 8 degrees Celsius and with little bruising or scarring appearing on skin.

Shipping quality: Considered very good. The fruit showed little bruising of the flesh or skin damage after normal harvesting and packing procedures. The fruit retained firmness and showed no internal breakdown of flesh or appreciable loss of eating quality under refrigeration at approximately 2 to 8 degrees Celsius indicates fruit should be highly acceptable for shipping.

Resistance to disease: High resistance to bacterial spot incited by *Xanthomonas campestris* pv. pruni. No unusual resistance or susceptibility to insects and diseases was noted.

COMPARISON WITH PARENTAL CULTIVARS

When 'Rich Joy' is compared to the female parent, 'Fameprince' (unpatented), the fruit are juicier, have more exterior red blush, and ripen 2 weeks earlier. When 'Rich Joy' is compared to the male parent, BY87P0943 (unpatented), an open pollinated seedling of 'Blazeprince' (unpatented), the fruit are sweeter, have richer flavor, have larger size, and ripen about 5-6 weeks later.

We claim:

1. A new and distinct variety of peach tree as illustrated and described, characterized by a high chilling requirement and bearing fruit having, yellow-fleshed fruit with normal acidity and melting, freestone with rich flavor and excellent eating quality a high percentage of red blush with an attractive yellow ground color, with fruit ripening in mid-July in Byron, Ga.

* * * * *